(12) United States Patent
Keighley

(10) Patent No.: US 9,907,885 B2
(45) Date of Patent: Mar. 6, 2018

(54) DEVICE

(75) Inventor: Michael Robert Burch Keighley, Tanworth-in-Arden (GB)

(73) Assignee: KEIGHLEYCOLO LTD, Solihull (GB)

( * ) Notice: Subject to any disclaimer, the term of this patent is extended or adjusted under 35 U.S.C. 154(b) by 695 days.

(21) Appl. No.: 14/005,989

(22) PCT Filed: Sep. 26, 2011

(86) PCT No.: PCT/GB2011/051810
§ 371 (c)(1),
(2), (4) Date: May 2, 2014

(87) PCT Pub. No.: WO2011/151659
PCT Pub. Date: Dec. 8, 2011

(65) Prior Publication Data
US 2014/0227337 A1    Aug. 14, 2014

(30) Foreign Application Priority Data
Mar. 21, 2011    (GB) .................................. 1104686.9

(51) Int. Cl.
| | | |
|---|---|---|
| A61B 17/04 | (2006.01) |
| A61L 31/16 | (2006.01) |
| A61B 17/00 | (2006.01) |
| A61L 27/54 | (2006.01) |
| A61L 27/58 | (2006.01) |
| A61L 31/06 | (2006.01) |
| A61L 31/10 | (2006.01) |
| A61B 17/06 | (2006.01) |
| A61M 27/00 | (2006.01) |

(52) U.S. Cl.
CPC .......... *A61L 31/16* (2013.01); *A61B 17/0057* (2013.01); *A61B 17/06066* (2013.01); *A61L 27/54* (2013.01); *A61L 27/58* (2013.01); *A61L 31/06* (2013.01); *A61L 31/10* (2013.01); *A61B 17/04* (2013.01); *A61B 17/0487* (2013.01); *A61B 17/06004* (2013.01); *A61B 17/06166* (2013.01); *A61B 2017/00004* (2013.01); *A61B 2017/00641* (2013.01); *A61B 2017/00884* (2013.01); *A61B 2017/00889* (2013.01); *A61B 2017/00893* (2013.01); *A61B 2017/06028* (2013.01); *A61B 2017/06085* (2013.01); *A61L 2300/404* (2013.01); *A61L 2300/41* (2013.01); *A61L 2300/414* (2013.01); *A61L 2300/426* (2013.01); *A61M 27/00* (2013.01)

(58) Field of Classification Search
CPC . A61B 17/0057; A61B 17/04; A61B 17/0487; A61B 17/06004; A61B 17/06066; A61B 17/06166; A61B 2017/00004; A61B 2017/00641; A61B 2017/00884; A61B 2017/00889; A61B 2017/00893; A61B 2017/06028; A61B 2017/06085; A61L 27/54; A61L 27/58; A61L 2300/404; A61L 2300/41; A61L 2300/414; A61L 2300/426; A61L 31/06; A61L 31/10; A61L 31/16; A61M 27/00
See application file for complete search history.

(56) References Cited

U.S. PATENT DOCUMENTS

| | | |
|---|---|---|
| 2005/0070759 A1 | 3/2005 | Armstrong |
| 2007/0031508 A1 | 2/2007 | Armstrong et al. |
| 2007/0129757 A1 | 6/2007 | Armstrong |
| 2008/0004657 A1 | 1/2008 | Obermiller et al. |
| 2008/0051831 A1* | 2/2008 | Deal ................ A61B 17/0057 606/213 |
| 2009/0069843 A1 | 3/2009 | Agnew |

FOREIGN PATENT DOCUMENTS

| | | |
|---|---|---|
| CN | 2676945 Y | 9/2005 |
| CN | 101134014 A | 3/2008 |
| ES | 2116914 A1 | 7/1998 |
| WO | WO 05/020823 A1 | 3/2005 |
| WO | WO 2005/020823 A | 3/2005 |

(Continued)

OTHER PUBLICATIONS http://ksef.kstc.com/dynamic/awards/round010.cfm dated by wayback machine as Jul. 3, 2008, see Razvan research project, linked to http://ksef.kstc.com/Dynamic/Awards/Abstract.cfm?ContactID=KSEF-1401-RDE-010 see summary of research.

(Continued)

*Primary Examiner* — Suzanne Ziska
(74) *Attorney, Agent, or Firm* — Alston & Bird LLP

(57) ABSTRACT

The present invention relates to devices and related methods for treating fistulas such as anal or recto-vaginal fistulas, in particular by the use of a seton to secure a tissue growth promoter such as a growth factor and/or fibrin. The various devices are particularly suitable for positioning tissue growth promoters securely within a fistula. Thus, one device comprises a seton and a tissue growth promoter. Further related aspects of the invention included devices comprising an enclosure provided in between portions of a seton, devices comprising a seton and a plurality of holes for enabling the device to be sutured to tissue, devices comprising a probe and a seton that are releasably connectable end-to-end, devices comprising an attachment device to secure the ends of a seton, and devices comprising a fistula plug adapted to be secured to a section.

21 Claims, 8 Drawing Sheets

(56) References Cited

FOREIGN PATENT DOCUMENTS

| WO | WO 05/096957 A1 | 10/2005 |
| WO | WO 2005/096957 A1 | 10/2005 |
| WO | WO 06/119256 A2 | 11/2006 |
| WO | WO 07/002260 A2 | 1/2007 |
| WO | WO 11/151659 A2 | 12/2011 |

OTHER PUBLICATIONS

"Seton Stitch", Wikipedia, the free encyclopedia, Medical Term for a Procedure Used to Aid the Healing of Fistulae, 1 page, (2011). [Retrieved from the Internet Jul. 10, 2014: <URL: http://en.wikipedia.org/w/index.php?title=Seton_stitch&oldid=413344285>].

WIPO Application No. PCT/GB2011/051810, International Preliminary Report on Patentability, dated Oct. 3, 2013.

WIPO Application No. PCT/GB2011/051810, International Search Report, dated Sep. 12, 2012.

WIPO Application No. PCT/GB2011/051810, Written Opinion of the International Searching Authority, dated Sep. 12, 2012.

\* cited by examiner

DEVICE

CROSS REFERENCE OF RELATED APPLICATION

This application is a US national phase under 35 USC 371 of PCT/GB2011/051810 filed Sep. 26, 2011, which claims priority to GB 1104686.9 filed Mar. 21, 2011.

FIELD OF THE INVENTION

The present invention relates to devices and related methods for treating fistulas such as anal or recto-vaginal fistulas, in particular by the use of a seton to secure a tissue growth promoter such as a growth factor and/or fibrin. The various devices are particularly suitable for positioning tissue growth promoters securely within a fistula. Thus, one device comprises a seton and a tissue growth promoter. Further related aspects of the invention include devices comprising an enclosure provided inbetween portions of a seton, devices comprising a seton and a plurality of holes for enabling the device to be sutured to tissue, devices comprising a probe and a seton that are releasably connectable end-to-end, devices comprising an attachment device to secure the ends of a seton, and devices comprising a fistula plug adapted to be secured to a seton.

BACKGROUND OF THE INVENTION

An anal fistula, otherwise known as an anorectal fistula, is an abnormal passage formed between the wall of the anal canal and the skin around the anus, typically the perianal skin. An anal fistula usually originates from an infection in an anal gland located in the anal canal. In the case of an anal gland becoming infected, an abscess may form deep under the skin around the anus which requires surgical drainage. After drainage, a tract between the drainage site and the wall of the anal canal may form resulting in an anal fistula. Fistulas cause intermittent symptoms of discharge and generally do not heal without treatment or surgical intervention. Anal fistulas are also a common feature of inflammatory bowel diseases, especially ulcerative colitis and Crohn's disease.

'Lay open' fistulotomy is the conventional surgery for treating an anal fistula and involves dividing the tissue between the fistula and the skin so as to promote tissue regeneration and hence healing of the fistula. A disadvantage with this procedure is that it causes discomfort and scarring, and usually results in some level of incontinence.

In an alternative procedure, a seton may be used which is passed through the track of the fistula by use of a fistula probe. The seton is a string preferably formed out of silicon or rubber that is typically threaded through an eye of the fistula probe. The probe is then passed through the track of the fistula pulling the seton along so that it extends through the entire length of the fistula. As the probe reaches the wall of the anal canal, the probe is passed through the anus and then removed from the seton such that the two loose ends of the seton can be tied together so as to form a loop. The seton is typically either left in place long-term and assists in draining any discharge from the fistula, or is tied tight to produce a slow form of fistulotomy, that is, division of tissues superficial to the fistula.

Suitable devices for use in such a procedure are described in the prior art. For example, patent application WO 2005/020823 describes a device for the treatment of anal fistulas comprising a probe attached to a drainage thread. The probe is used to guide the drainage thread through the fistula, after which the probe may be removed and the two ends of the thread tied together. The thread acts to ensure that the fistula channel is kept open, allowing adequate drainage.

In some cases, particularly Crohn's disease, when the fistula becomes infected, it may be necessary for the patient to undergo a course of antibiotics and/or anti inflammatory medication prior to surgical treatment. Consequently, surgical treatment of the fistula is delayed causing discomfort. In an attempt to overcome this problem, Razvan Arsenescu has proposed the development of a biodegradable seton made from PLGA that releases an anti-inflammatory drug in a controlled fashion (see the proposal for an award from the Kentucky Science & Engineering Foundation entitled "Drug Eluting Biodegradable Seton for Treatment of Perianal Fistulas in Crohn's Disease" at http://ksef.kstc.com/Dynamic/Awards).

A problem with the conventional technique is that the knot of the seton is external to the body and may cause discomfort as the patient sits down. In some cases the knot becomes undone causing the seton to fall out of the fistula and so the process of inserting the seton needs to be repeated.

A further problem is that whilst movement of the seton within the fistula is desirable to assist in drainage, such movement may act to prevent tissue regeneration and hence healing of the fistula. Further surgical steps to close the fistula are therefore often required after the elimination of the infection.

As already indicated, an alternative to the above procedure is that the seton can be used to gradually divide the tissue superficial to the fistula. In this alternative procedure, the structures superficial to the fistula, such as the skin, subcutaneous fat and sphincter muscle, are slowly divided by tying the seton tightly. The process of gradual tightening causes the seton to divide the tissue it surrounds thereby promoting tissue regeneration and healing of the fistula. Unfortunately, this often results in some impairment of continence.

A device suitable for use in such a procedure is described in patent application WO 2005/096957. The device describes a silicone thread with either a transversal through hole at its tip or a tip-piece that includes a transversal through hole. Also provided is a removable supporting jacket which serves to guide the thread through the fistula. Once the thread has been passed through the fistula, the supporting jacket is removed and the distal end of the thread is passed through the transversal through hole at the tip. Fastening nodes may be provided along the length of the thread so as to interfere with the internal diameter of the transversal through hole, thus tying the thread. When tied tightly, a slow cutting action is provided resulting in the opening-up, or "elastic traction" of the fistula. In use, as the loop slackens due to the cutting action, more of the thread along with further fastening nodes may be pulled through the transversal through hole so as to ensure that the cutting action is maintained.

The main disadvantage of dividing the tissue in this way is that it tends to result in some level of incontinence. Furthermore, the lose ends of the thread may again cause discomfort as a patient sits down, and rotation of the tightened thread through the fistula may cause additional discomfort and risk of infection.

As fistulas vary in configuration, complexity and length, surgeons have to take great care when inserting a probe and seton through the track of a fistula as surrounding tissue can easily be damaged as a result of the probe going off course.

Furthermore, a seton is typically attached to the probe by the seton being inserted through an eye of the probe, or by an end of the seton overlapping an end of the probe and the ends being lashed together using a thread. These types of connections are bulky and may cause the seton to abrade or damage surrounding tissue as the seton is pulled through the fistula. Furthermore, it is also apparent that these configurations are often inadequate at maintaining the seton attached to the probe because the seton may become detached from the probe as it is pulled through the fistula. In such cases, the surgeon would need to repeat the procedure which potentially causes more trauma to the surrounding tissue and the patient.

In an attempt to avoid fistulotomy (the division of tissues superficial to the fistula track), an alternative recent procedure using a fibrin plug has been introduced. The fibrin plug comprises a scaffold of polymeric fibrin that is inserted into the fistula tract so as to promote tissue in-growth into the scaffold so as to restore natural tissue healing and formation.

A disadvantage with the fibrin plug and even its more recent modifications is that it tends to fall out of the fistula before the end of the 4 to 6 week healing process. Although the fibrin plug can be sutured to an inner wall of the anus to mitigate against this problem, this has proven to be insufficient to maintain the plug in position.

In an attempt to overcome the above disadvantages, a modified fibrin plug is disclosed in US patent application US 2007/0031508. The modified fibrin plug includes end caps and/or a "tail" which may be sutured to the patient after placement of the plug so as to secure the plug in position. Such a device again relies entirely on the strength of the sutures and surrounding tissue. Thus, whilst this represents an improvement on the conventional fibrin plug, it does not reliably overcome the problem of plug displacement.

There is also a need for devices that will enable other types of fistulas to be treated.

Such fistulas include for instance recto-vaginal fistulas, which are abnormal passages between the rectum and the vagina. These are particularly difficult to treat by conventional surgery. Recto-vaginal fistulas frequently recur requiring multiple operations resulting in bowel incontinence, pain and deformity. Recto-vaginal fistulas have become a bigger problem of late due to a rising incidence of inflammatory bowel disease (especially Crohn's disease), as well as operations to preserve continence for ulcerative colitis sufferers, by restorative proctocolectomy and ileal pouch anal anastomosis. Such procedures are also being performed on patients suffering from a variety of premalignant conditions. There is therefore a need for devices and procedures which will give a high chance of achieving primary healing in recto-vaginal fistulas without invasive surgical intervention.

The present invention seeks to provide a device that overcomes or substantially alleviates the problems mentioned above.

SUMMARY OF THE INVENTION

According to a first aspect of the present invention, there is provided a device comprising a seton suitable for treating a fistula, wherein the device comprises a tissue growth promoter. Preferably the seton comprises a tissue growth promoter.

The tissue growth promoter may comprise or be a tissue growth promoting agent, i.e. a pharmaceutical substance which encourages tissue growth such as a growth factor. Suitable growth factors include but are not limited to basic fibroblast growth factor (FGF-2), transforming growth factor beta (TGF-beta), epidermal growth factor (EGF), cartilage derived growth factor (CDGF), platelet derived growth factor (PDGF), insulin-like growth factors I and II (IGF-I and IGF-II), interferons (e.g. interferon $\alpha$, $\beta$, $\gamma$) and the like.

Alternatively the tissue growth promoter may comprise or be a tissue growth promoting matrix, i.e. a substance or structure which may act as a scaffold onto which and/or through which tissue may grow. Preferably tissue may grow both onto and through the scaffold.

In one embodiment of the first aspect of the present invention, the tissue growth promoting matrix comprises a microscopic scaffold, i.e. the scaffold structure is not visible to the naked eye. For instance, the scaffold may comprise a plurality of fibrils which may be non-interwoven or preferably interwoven and/or interconnected. Said fibrils may be interwoven and/or interconnected in an ordered or disordered structure.

Where a scaffold comprises a plurality of fibrils, preferably said fibrils have a diameter of from 0.1 nm to 1000 nm, more preferably from 1 nm to 500 nm, and most preferably from 10 nm to 100 nm.

Typically, where a scaffold comprises a plurality of fibrils, at least 10% by volume of the scaffold is occupied by the fibrils. Preferably at least 25% by volume, and more preferably at least 50% by volume of the scaffold is occupied by the fibrils.

In another embodiment of the first aspect of the present invention the tissue growth promoting matrix comprises a macroscopic scaffold, i.e. the scaffold structure is visible to the naked eye. For instance, the scaffold may comprise a plurality of interwoven and/or interconnected strands. Said strands may be interwoven and/or interconnected in an ordered or disordered structure.

In another embodiment, the scaffold may comprise a plurality of non-interwoven strands, such as a plurality of strands affixed to a central core, for example in a brush-like array. Preferably said strands are afixed substantially perpendicularly from the central core. Preferably the central core is the seton.

Where a macroscopic scaffold comprises a plurality of strands, preferably said strands have a diameter of from 1 $\mu$m to 1 mm, more preferably from 10 $\mu$m to 100 $\mu$m.

Typically, where a scaffold comprises a plurality of strands, at least 10% by volume of the scaffold is occupied by the strands. Preferably at least 25% by volume, and more preferably at least 50% by volume of the scaffold is occupied by the strands.

In one embodiment, the macroscopic scaffold comprises at least 10 strands per $cm^3$. Preferably, the macroscopic scaffold comprises at least 100 strands per $cm^3$. More preferably the macroscopic scaffold comprises at least 1000 strands per $cm^3$.

Alternatively, the scaffold may comprise a porous structure such as a sponge-like structure. Said porous structure may be microscopic or macroscopic.

Optionally, the tissue growth promoting matrix may comprise both a macroscopic scaffold and a microscopic scaffold. In a preferred embodiment, the macroscopic scaffold is made from, coated with or embedded in a microscopic scaffold. For instance, the strands and/or porous structure of the macroscopic scaffold may comprise a microscopic scaffold.

In one embodiment of the first aspect of the present invention, at least 10% by volume of the tissue growth promoting matrix is void. Preferably at least 25% by volume, and more preferably at least 50% by volume of the tissue growth promoting matrix is void.

The material from which the tissue growth promoting matrix is made may be biological or non-biological, or a mixture thereof. Preferably the material promotes tissue remodelling and/or is remodelable. Preferably the material promotes angiogenesis.

In a preferred embodiment of the first aspect of the present invention, the tissue growth promoting matrix is made from biocompatible materials.

As used herein, the term "biocompatible materials" refers to materials which do not have unacceptable adverse effects on the subject (e.g. human or other animal) to be treated. Preferably the biocompatible materials do not have unacceptable adverse effects on the subject to be treated when left in contact with the subject for at least two weeks, more preferably for at least 4 weeks, and most preferably for at least 6 weeks.

In one embodiment of the first aspect of the present invention, the tissue growth promoting matrix comprises a biological material and/or a synthetic equivalent thereof. Preferably the biological material and/or the synthetic equivalent thereof is fibrous. Preferably, where the tissue growth promoting matrix comprises a microscopic scaffold, the microscopic scaffold comprises a biological material and/or a synthetic equivalent thereof.

The biological material may be xenogeneic, allogeneic (e.g. cadaveric), autogeneic, or a mixture thereof.

Typically, where the tissue growth promoting matrix comprises a biological material, the biological material is processed and/or purified, preferably so that the biological material is non-cellular.

Suitable substances which can provide a scaffold for tissue growth include fibrin; collagens such as Type I, Type II, Type III, Type IV or Type V collagen; other extracted collagenous extracellular matrix (ECM) materials such as submucosa tissue (e.g. intestinal submucosa, urinary bladder submucosa or uterine submucosa), fascial tissue, renal capsule membrane tissue, dermal tissue (e.g. dermal collagen), dura mater, pericardium tissue, serosa, peritoneum, basement membrane layers and the like.

Other suitable substances which can provide a scaffold for tissue growth include fibrous biological materials or synthetic equivalents thereof which have been cross-linked, for example using cross-linking agents such as dialdehydes, polyepoxides, dichloroalkanes and the like to give material such as albumin crossed linked with glutaraldehyde. Cross-linking may also be achieved by the reaction of chemical groups within the fibrous biological materials or synthetic equivalents thereof, such as by dehydration, the formation of disulphide bridges and the like.

In a particularly preferred embodiment, the tissue growth promoting matrix is made from fibrin and/or collagen. Preferably, where the tissue growth promoting matrix comprises a microscopic scaffold, the microscopic scaffold comprises fibrin and/or collagen. Most preferably, the tissue growth promoting matrix is made from fibrin.

As used herein, "fibrin" refers to a polymer formed from fibrin monomers, which themselves have been formed by the treatment of fibrinogen with thrombin.

In one embodiment of the first aspect of the present invention, the tissue growth promoting matrix comprises a biodegradable material. Preferably where the tissue growth promoting matrix comprises a macroscopic scaffold, the material from which the macroscopic scaffold is made is biodegradable, such as a biodegradable polymer.

Alternatively or in addition, the tissue growth promoting matrix may comprise a non-biodegradable material such as a non-biodegradable polymer. Preferably, where the tissue growth promoting matrix comprises a non-biodegradable material, the tissue growth promoting matrix comprises a macroscopic scaffold and the macroscopic scaffold comprises the non-biodegradable material.

As used herein, a "biodegradable material" refers to a material that decomposes on contact with biological fluids or systems such as blood plasma, skin or sphincter muscle. Similarly a "biodegradable polymer" refers to a polymer that undergoes hydrolysis on contact with biological fluids or systems such as blood plasma, skin or sphincter muscle. Conversely a "non-biodegradable" material or polymer refers to a material or polymer that does not substantially decompose or undergo hydrolysis on contact with biological fluids or systems. A polymer that is "entirely biodegradable" refers to a polymer wherein at least one covalent bond in every link between constituent monomer units is able to undergo hydrolysis on contact with biological fluids or systems.

In one embodiment of any aspect of the present invention, a "biodegradable" material or polymer decomposes or undergoes hydrolysis on contact with an aqueous solution of pH between 5 and 9, preferably between 6 and 8, more preferably about 7.

Preferably a "biodegradable" material or polymer undergoes decomposition or hydrolysis on contact with biological fluids or systems at a rate such that it takes on average at least 10 days for the material or polymer to degrade into its constituent non-biodegradable sections and/or constituent monomer units. More preferably it takes on average at least 20 days, at least 30 days or at least 40 days for the material or polymer to degrade into its constituent non-biodegradable sections and/or constituent monomer units. Most preferably it takes on average at least 50 days for the material or polymer to degrade into its constituent non-biodegradable sections and/or constituent monomer units.

Preferably a "biodegradable" material or polymer undergoes decomposition or hydrolysis on contact with biological fluids or systems at a rate such that it takes on average less than 400 days for the material or polymer to degrade into its constituent non-biodegradable sections and/or constituent monomer units. More preferably it takes on average less than 200 days for the material or polymer to degrade into its constituent non-biodegradable sections and/or constituent monomer units. Most preferably it takes on average less than 100 days for the material or polymer to degrade into its constituent non-biodegradable sections and/or constituent monomer units.

Biodegradable polymers suitable for use in the present invention include but are not limited to polyesters such as poly-lactic acids, poly-lactides, polyglycolic acid, polyglycolides, polycaprolactones, polycaprolactone diols, and polycaprolactone triols; polyanhydrides such as poly(sebacic acids), poly(adipic acids), poly(fumaric anhydrides), poly(stilbene dicarboxylic acid anhydrides) and poly[1,6-bis-carboxy-phenoxy)hexane]; polyphosphoesters such as poly[1,4-bis(hydroxyethyl)-terephthalate-alt-ethyloxyphosphate]; polyphosphazenes such as poly(bis(1,4-dioxapentyl) phosphazenes), poly(bis(4-carboxyphenoxy)phosphazenes) and poly-[bis(1-(ethoxycarbonyl)-2-phenylethylamino) phosphazene]; polyethers such as polypropylene oxides and polyethylene glycols; other synthetic polymers such as polycarbonates, polycyanoacrylates, polydioxanones, poly(1,5-dioxepan-2-one), polyaminoacids, polyamides, polyhydroxybutyrates, polyhydroxyvalerates, polyesteramides, polyvinyl pyrrolidone, polyurethanes, polyalkylene succinates, poly(malic acid), polyalkylene oxalates, polyorthocarbonates, polyorthoesters, polyamines, polyhydroxycelluloses, polyvinyl alcohol, polyacetals, polyketals and cyclodextrins; and natural polymers such as albumin, chitin, chitosan, collagen, dextran, fibrin, fibrinogen, gelatine, polysaccharides, carrageenan, tragacanth, acacia, xanthan gum and poly(alginic acid).

Biodegradable polymers can also include copolymers of any of the above, including alternating copolymers, periodic copolymers, random copolymers and block copolymers. Examples of such copolymers include poly(lactic acid-co-glycolic acids), poly(lactide-co-glycolides), poly(lactide-co-caprolactones), poly(lactide-co-caprolactone-co-glycolide), poly[(lactide-co-ethylene glycol)-co-ethyloxyphosphate], poly[(1,6-bis-carboxyphenoxy)hexane)-co-sebacic acid], poly(hydroxybutyric acid-co-hydroxyvaleric acid), poly[1,4-bis(hydroxyethyl) terephthalate-alt-ethyloxy-phosphate]-co-1,4-bis(hydroxyethyl) terephthalate-co-terephthalate, poly(ethylene glycol)-poly(caprolactone) methyl ether block copolymers, poly(ethylene glycol)-polylactide methyl ether block copolymers, poly(ethylene glycol)methyl ether-polylactide polylactide block copolymers, poly(ethylene oxide)-polycaprolactone block copolymers, poly(ethylene oxide)-polylactide block copolymers, polycaprolactone-polytetrahydrofuran-polycaprolactone block copolymers, polylactide-poly(ethylene glycol)-polylactide block copolymers, and polyoxyethylene-polypropylene block copolymers.

Suitable non-biodegradable polymers for use in the present invention include celluloses such as cellulose ethers, ethyl celluloses, hydroxypropyl methyl celluloses, hydroxypropyl celluloses, hydroxyethyl celluloses, hydroxyethylmethyl celluloses, methyl celluloses, cellulose acetates and their derivatives and copolymers thereof. Other suitable non-biodegradable polymers include polyacrylates, polymethacrylates, polypyrrolidones, polyoxyethylenes, polyoxyethylene-polypropylene copolymers, polymethylmethacrylatyes, polybutylmethacrylates, polysiloxanes, shellac, acrylic and methacrylic acid based polymers, and copolymers thereof.

In a further embodiment of the first aspect of the present invention, the tissue growth promoter may comprise one or more tissue growth promoting matrix precursors, i.e. substances which are able to react to form a tissue growth promoting matrix. For instance, the tissue growth promoter may be in the form of two or more agents which together are able to form a tissue growth promoting matrix, such as fibrinogen and thrombin.

The tissue growth promoter may also comprise a combination of one or more tissue growth promoting agents, one or more tissue growth promoting matrices, and/or agents which together are able to form tissue growth promoting matrices. For instance, the tissue growth promoter may comprise a combination of a tissue growth promoting matrix and a tissue growth promoting agent; for example fibrin and a growth factor.

Optionally the tissue growth promoting matrix may be coated or impregnated with one or more tissue growth promoting agents, and/or one or more tissue growth promoting matrix precursors, and/or other pharmaceutical agents.

In one embodiment of the first aspect of the present invention, a segment or all of the seton comprises or consists of a tissue growth promoting matrix. Preferably the segment to be positioned within the fistula comprises or consists of a tissue growth promoting matrix.

In another embodiment of the first aspect of the present invention, a tissue growth promoting matrix is attached to the seton. For instance, the seton may be thread through a tissue growth promoting matrix such as a fibrin plug. Optionally, in such an embodiment, the seton itself does not comprise a tissue growth promoter.

Where the seton is thread through a tissue growth promoting matrix such as a fibrin plug, the tissue growth promoting matrix may be securely attached such that movement of the tissue growth promoting matrix along the length of the seton is prevented. Alternatively, the tissue growth promoting matrix may be free to move along the length of the seton. Alternatively still the tissue growth promoting matrix may be a friction fit on the seton, such that it may be moved along the length of the seton only by the application of a force greater than gravity, such as hand force.

Optionally, two or more tissue growth promoting matrices such as fibrin plugs may be attached to the seton.

In a further embodiment of the first aspect of the present invention, a tissue growth promoter is coated on the seton, preferably such that tissue growth promoter is released immediately on contact with the patient. Preferably in such an embodiment the tissue growth promoter is a tissue growth promoting agent and/or a tissue growth promoting matrix precursor.

In yet another embodiment of the first aspect of the present invention, a tissue growth promoter is impregnated or encapsulated within part or all of the seton, preferably such that the tissue growth promoter is released in a delayed and/or sustained manner. For instance, the tissue growth promoter may be impregnated or encapsulated within the seton itself, or within a coating provided upon the seton. Again, preferably in such an embodiment the tissue growth promoter is a tissue growth promoting agent and/or a tissue growth promoting matrix precursor.

Optionally, the device of the first aspect of the present invention may further comprise one or more additional pharmaceutical agents. The one or more additional pharmaceutical agents are preferably selected from anti-inflammatories, antibacterial agents, immunomodulators or combinations thereof.

In one embodiment the anti-inflammatory is a COX inhibitor. As used herein, a 'COX inhibitor' refers to an inhibitor of cyclooxygenase. For instance, the COX inhibitor may be a non-steroidal anti-inflammatory drug (NSAID). Preferably said NSAID is selected from:

(a) an aminoarylcarboxylic acid derivative such as enfenamic acid, etofenamate, flufenamic acid, isonixin, meclofenamic acid, mefenamic acid, niflumic acid, talniflumate, terofenamate or tolfenamic acid;

(b) an arylacetic acid derivative such as aceclofenac, acemetacin, alclofenac, amfenac, amtolmetin guacil, bromfenac, bufexamac, diclofenac, etodolac, felbinac, fenclozic acid, fentiazac, glucametacin, ibufenac, indomethacin, isoxepac, lonazolac, metiazinic acid, mofezolac, nepafenac, oxametacine, proglumetacin, sulindac, tiaramide, tolmetin, tropesin or zomepirac;

(c) an arylbutyric acid derivative such as bumadizon, butibufen, butixirate or fenbufen;

(d) an arylcarboxylic acid derivative such as ketorolac or tinoridine;

(e) an arylpropionic acid derivative such as alminoprofen, bermoprofen, carprofen, fenoprofen, flunoxaprofen, flurbiprofen, ibuprofen, ibuproxam, ketoprofen, loxoprofen, naproxen, oxaprozin, piketoprofen, pranoprofen, suprofen, tiaprofenic acid, ximoprofen or zaltoprofen;

(f) a pyrazole derivative such as difenamizole or epirizole;

(g) a pyrazolone derivative such as apazone, feprazone, mofebutazone, morazone, oxyphenbutazone, phenylbutazone, pipebuzone, propyphenazone, ramiphenazone or suxibuzone;
(h) a salicylic acid derivative such as acetaminosalol, aspirin, balsalazide, benorylate, diflunisal, fendosal, gentisic acid, glycol salicylate, imidazole salicylate, lysine acetylsalicylate, mesalamine, morpholine salicylate, 1-napthyl salicylate, olsalazine, parsalmide, phenyl acetylsalicylate, phenyl salicylate, salicylamide O-acetic acid, salicylsulphuric acid, salsalate, salicylic acid or sulfasalazine;
(i) a thiazinecarboxamide derivative such as ampiroxicam, lornoxicam, meloxicam, piroxicam or tenoxicam;
(j) a selective COX-2 inhibitor such as celecoxib, etoricoxib, lumiracoxib, parecoxib, rofecoxib or valdecoxib; or
(k) another NSAID such as ε-acetamidocaproic acid, S-adenosylmethionine, ajulemic acid, 3-amino-4-hydroxybutyric acid, bendazac, benzydamine, α-bisabolol, bucolome, difenpiramide, ditazol, emorfazone, fepradinol, guaiazulene, lexipafant, licofelone, nabumetone, nimesulide, oxaceprol, perisoxal, proquazone, superoxide dismutase or tenidap.

In a preferred embodiment, said NSAID is an arylpropionic acid derivative such as ibuprofen or naproxen. In another preferred embodiment, said NSAID is a selective COX-2 inhibitor.

In another embodiment, the anti-inflammatory is a steroid. Preferably the steroid is a corticosteroid such as 21-acetoxypregnenolone, fludrocortisone, fluticasone furoate, fluticasone propionate, alclometasone, algestone, amcinonide, beclomethasone, betamethasone, budesonide, chloroprednisone, ciclesonide, clobestasol, clobetasone, clocortolone, cloprednol, cortisone, cortivazol, deflazacort, desonide, desoximetasone, dexamethasone, diflorasone, diflucortolone, difluprednate, enoxolone, etiprednol dicloacetate, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisone, predrival, prednylidene, rimexolone, tixocortol, triamcinolone, triamcinolone acetonide, triamcinolone benetonide or triamcinolone hexacetonide.

Most preferably, the steroid is selected from hydrocortisone, betamethasone, cortisone, deflazacort, dexamethasone, methylprednisolone, prednisolone, triamcinolone, fludrocortisone, beclomethasone, budesonide, ciclesonide, fluticasone furoate, mometasone furoate, flunisolide, flumethasone, fluorometholone or loteprednol etabonate.

In yet another embodiment, the anti-inflammatory is an anti-interleukin-6 agent such as tocilizumab, elsilimomab, anti-IL-6 chimeric monoclonal antibody, ALD518 or CNTO 136. Preferably the anti-interleukin-6 agent is tocilizumab.

In yet another embodiment, the anti-inflammatory is a TNF inhibitor. The TNF inhibitor may be for instance a monoclonal antibody such as infliximab, adalimumab, certolizumab pegol or golimumab, a circulating receptor fusion protein such as etanercept, or a xanthine derivative such as pentoxifylline or bupropion. In one embodiment of the first aspect of the present invention, the antibacterial agent is an antibiotic. The antibiotic may be selected from:
(a) aminoglycosides such as amikacin, arbekacin, bambermycins, butirosin, dibekacin, dihydrostreptomycin, fortimicins, gentamicin, isepamicin, kanamycin, micronomicin, neomycin, netilmicin, paromomycin, ribostamycin, sisomicin, spectinomycin, streptomycin or tobramycin;
(b) amphenicols such as azidamfenicol, chloramphenicol or thiamphenicol;
(c) ansamycins such as rifamide, rifampin, rifamycin SV, rifapentine or rifaximin;
(d) β-lactams including carbacephems such as loracarbef; carbapenems such as biapenem, doripenem, ertapenem, imipenem, meropenem or panipenem; cephalosporins such as cefaclor, cefadroxil, cefamandole, cefatrizine, cefazedone, cefazolin, cefcapene pivoxil, cefdinir, cefditoren, cefepime, cefetamet, cefixime, cefmenoxime, cefodizime, cefonicid, cefoperazone, ceforanide, cefoselis, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftobiprole medocaril, ceftriaxone, cefuroxime, cefuzonam, cephacetrile sodium, cephalexin, cephaloglycin, cephaloridine, cephalosporin C, cephalothin, cephapirin sodium, cephradine or pivcefalexin; cephamycins such as cefbuperazone, cefmetazole, cefminox, cefotetan or cefoxitin; monobactams such as aztreonam or carumonam; oxacephems such as flomoxef or moxalactam; penems such as faropenem or ritipenem; and penicillins such as amdinocillin, amdinocillin pivoxil, amoxicillin, ampicillin, apalcillin, asp oxicillin, azidocillin, azlocillin, bacampicillin, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin, oxacillin, penamecillin, penethamate hydriodide, penicillin G, penicillin G benzathine, penicillin G procaine, penicillin N, penicillin O, penicillin V, phenethicillin potassium, piperacillin, pivampicillin, propicillin, quinacillin, sulbenicillin, sultamicillin, talampicillin, temocillin or ticarcillin;
(e) lincosamides such as clindamycin or lincomycin;
(f) macrolides such as azithromycin, cethromycin, clarithromycin, dirithromycin, erythromycin, erythromycin ethylsuccinate, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, telithromycin or troleandomycin;
(g) polypeptides such as amphomycin, bacitracin, bacitracin zinc, capreomycin, colistin, dalbavancin, daptomycin, enduracidin, enviomycin, fusafungine, gramicidin(s), gramicidin S, iseganan, oritavancin, polymyxin, quinupristin, ramoplanin, ristocetin, teicoplanin, telavancin, thiostrepton, tuberactinomycin, tyrocidine, tyrothricin, vancomycin or viomycin;
(h) tetracyclines such as chlortetracycline, clomocycline, demeclocycline, doxycycline, guamecycline, lymecycline, meclocycline, methacycline, minocycline, oxytetracycline, pipacycline, rolitetracycline, tetracycline or tigecycline; or
(i) other antibiotics such as cycloserine, dalfopristin, fosfomycin, fusidic acid, mupirocin, pristinamycin or virginiamycin.

Preferably the antibiotic is selected from amikacin, gentamicin, neomycin, tobramycin, cefaclor, cefadroxil, cephalexin, cefixime, cefotaxime, cefpodoxime proxetil, cephradine, ceftazidime, ceftriaxone, cefuroxime, azithromycin, clarithromycin, erythromycin, erythromycin ethylsuccinate, erythromycin stearate, telithromycin, amoxicillin, ampicillin, floxacillin, penicillin G, penicillin V, piperacillin, ticarcillin, rifampin, demeclocycline, doxycycline, lymecycline, minocycline, oxytetracycline, tetracycline, aztreonam, chloramphenicol, clindamycin, colistin, daptomycin, doripenem, ertapenem, imipenem, meropenem, quinupristin, dalfopristin, fusidic acid, teicoplanin, tigecycline or vancomycin.

In another embodiment, the antibacterial agent is a synthetic antibacterial agent. The synthetic antibacterial agent may be selected from:

(a) 2,4-diaminopyrimidines such as brodimoprim, tetroxoprim or trimethoprim;

(b) nitrofurans such as furaltadone, furazolium chloride, nifuratel, nifurfoline, nifurpirinol, nifurtoinol or nitrofurantoin;

(c) oxazolidinones such as linezolid;

(d) quinolones and analogs thereof such as balofloxacin, cinoxacin, ciprofloxacin, clinafloxacin, enoxacin, fleroxacin, flumequine, garenoxacin, gatifloxacin, gemifloxacin, grepafloxacin, levofloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, prulifloxacin, rosoxacin, rufloxacin, sitafloxacin, sparfloxacin, tosufloxacin or trovafloxacin;

(e) sulfonamides such as acetyl sulfamethoxypyrazine, chloramine-B, chloramine-T, dichloramine T, $N^2$-formylsulfisomidine, mafenide, noprylsulfamide, phthalylsulfacetamide, phthalylsulfathiazole, salazosulfadimidine, succinylsulfathiazole, sulfabenzamide, sulfacetamide, sulfachloropyridazine, sulfachrysoidine, sulfacytine, sulfadiazine, sulfadicramide, sulfadoxine, sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, $N^4$-sulfanilylsulfanilamide, sulfanilylurea, N-sulfanilyl-3,4-xylamide, sulfaperine, sulfaphenazole, sulfaproxyline, sulfapyrazine, sulfapyridine, sulfathiazole, sulfathiourea, sulfisomidine or sulfisoxazole;

(f) sulfones such as acediasulfone, dapsone, glucosulfone sodium, solasulfone, succisulfone, sulfanilic acid, p-sulfanilylbenzylamine, sulfoxone sodium or thiazolsulfone; or (g) other synthetic antibacterial agents such as clofoctol, methenamine, metronidazole, nitroxoline, noxythiolin, pexiganan, taurolidine, tinidazole or xibornol.

Preferably the synthetic antibacterial agent is selected from metronidazole, tinidazole, ciprofloxacin, levofloxacin, ofloxacin, moxifloxacin, nalidixic acid, trimethoprim, sulfamethoxazole, linezolid or noxythiolin.

In a further embodiment, the antibacterial agent is an anti-rickettsial agent such as p-aminobenzoic acid, chloramphenicol or tetracycline.

In yet another embodiment, the antibacterial agent is an antibacterial adjunct. Preferably the antibacterial adjunct is a β-lactamase inhibitor such as clavulanic acid, sulbactam, sultamicillin or tazobactam. More preferably, the antibacterial adjunct is selected from clavulanic acid or tazobactam.

In one embodiment of the first aspect of the present invention, the immunomodulator is selected from acemannan, actimid, aldesleukin, amiprilose, ampligen, bucillamine, ditiocarb sodium, glatiramer, imiquimod, inosine pranobex, interferon-β, interferon-γ, leflunomide, lenalidomide, lentinan, levamisole, lisofylline, macrophage colony-stimulating factor, mitoxantrone, pidotimod, platonin, polyoxidonium, procodazole, propagermanium, resiquimod, romurtide, teriflunomide, thalidomide, thymalfasin, thymomodulin, thymopentin, thymostimulin, ubenimex or Virulizin®.

Alternately, the immunomodulator may be an immunosuppressant, such as abatacept, abetimus sodium, alefacept, alemtuzumab, azathioprine, basiliximab, belatacept, brequinar, cyclosporins, daclizumab, efalizumab, everolimus, fingolimod, gusperimus, 6-mercaptopurine, mizoribine, muromonab CD3, mycophenolic acid, pimecrolimus, rapamycin or tacrolimus.

In one embodiment of the first aspect of the present invention, the one or more additional pharmaceutical agents are coated on the seton, preferably such that the one or more additional pharmaceutical agents are released immediately on contact with the patient.

In another embodiment, the one or more additional pharmaceutical agents are impregnated or encapsulated within part or all of the seton, preferably such that the one or more additional pharmaceutical agents are released in a delayed and/or sustained manner.

Where a tissue growth promoter or pharmaceutical agent is released in a sustained manner, preferably the tissue growth promoter or pharmaceutical agent is released over a period of from 1 to 400 days. More preferably the tissue growth promoter or pharmaceutical agent is released over a period of from 7 to 100 days. Most preferably the tissue growth promoter or pharmaceutical agent is released over a period of from 25 to 50 days.

In certain embodiments of the first aspect of the present invention, the tissue growth promoter or pharmaceutical agent may be impregnated within a non-biodegradable polymer matrix, preferably such that the tissue growth promoter or pharmaceutical agent is able to leach out of the matrix over a period of time.

In some embodiments of the first aspect of the present invention, the seton comprises a biodegradable material such as a biodegradable polymer. Preferably the biodegradable polymer is selected from a polyester, a polyanhydride, a polyphosphoester, a polyphosphazene or a polyether.

In one embodiment of the first aspect of the present invention, all of the seton is made from a biodegradable material.

In another embodiment of the first aspect of the present invention, part of the seton is made from a biodegradable material. Preferably the remainder of the seton is made from a pharmaceutical agent (such as a tissue growth promoter) and/or a non-biodegradable material.

For instance, a segment of the seton to be positioned within the fistula may be biodegradable. Thus, this segment may slowly biodegrade over time once the seton is inserted, eventually causing the seton loop to break and the seton to fall out. The need for surgical removal of the seton is thereby obviated.

Alternatively the device may comprise a tissue growth promoting matrix such as a fibrin plug located inbetween biodegradable portions of the seton. Thus, in use tissue growth into the matrix and biodegradation of the connecting portions of the seton simultaneously occur. Accordingly, the tissue growth promoting matrix is held in place by the remainder of the seton long enough for it to become attached to the surrounding tissue of the patient, by which time the connecting portions of the seton have degraded, causing the remainder of the seton to break free from the tissue growth promoting matrix and fall out of the patient.

Similarly, where the seton is thread through a tissue growth promoting matrix such as a fibrin plug, the portion of the seton passing through the tissue growth promoting matrix may be biodegradable.

In other embodiments of the first aspect of the present invention, the tissue growth promoter or pharmaceutical agent may be impregnated or encapsulated within the biodegradable material. Accordingly, the tissue growth promoter or pharmaceutical agent may then be able to leach out of the biodegradable material over a period of time and/or be released as the biodegradable material degrades.

A second aspect of the present invention provides a seton suitable for treating a fistula, wherein the device further comprises an enclosure provided inbetween portions of the seton. Preferably said enclosure provides access means for placing a substance such as a pharmaceutical agent within the enclosure. For instance, two halves of the enclosure may unscrew to allow access thereto. Alternatively, one or more ends of the enclosure may unscrew from the seton at the point of attachment, so as to allow access to the inside of the enclosure.

Alternatively still, the enclosure may be sealed on manufacture with a substance such as a pharmaceutical agent provided therein.

In one embodiment, the enclosure is formed of a permeable wall such as a mesh wall. Conveniently, the seton and/or any wall of the enclosure are made from a biodegradable material, such as any outlined for use in relation to the first aspect of the present invention.

Alternatively, the seton and/or any wall of the enclosure may be made from a non-biodegradable material, such as any non-biodegradable polymer outlined for use in relation to the first aspect of the present invention.

In one embodiment of the second aspect of the present invention, one or more walls of the enclosure are made from a biodegradable material and the remainder of the seton is made from a non-biodegradable material.

Preferably, the enclosure is loaded with one or more pharmaceutical agents, such as a tissue growth promoter and/or any other pharmaceutical agent as outlined for use in relation to the first aspect of the present invention. For instance a tissue growth promoting matrix, such as a fibrin plug or fibrin pellets, may be inserted into the enclosure.

In another embodiment of the second aspect of the present invention, the seton and/or any wall of the enclosure is coated or impregnated with one or more tissue growth promoting agents, and/or one or more tissue growth promoting matrix precursors, and/or other pharmaceutical agents, such as any outlined for use in relation to the first aspect of the present invention.

According to a third aspect of the present invention, there is provided a device comprising a seton suitable for treating a fistula, wherein the device comprises a plurality of holes for enabling the device to be sutured to tissue. Such a device is particularly suitable for use in securing a tissue growth promoter within a fistula since it enables the seton to be fixed tightly in place, preventing displacement of the seton loop and hence preventing the tissue growth promoter from sliding out of the fistula as the seton loop becomes displaced.

In one embodiment of the third aspect of the present invention the seton comprises a plurality of holes for enabling the device to be sutured to tissue. Alternatively or in addition, another part of the device such as an attachment device as discussed below may be provided with a plurality of holes for enabling the device to be sutured to tissue.

In a preferred embodiment of the third aspect of the present invention, the device is also a device according to the first and/or second aspect of the present invention.

In one embodiment of any of the first to third aspects of the present invention, the device further comprises a probe, wherein the probe and the seton are connectable together end-to-end.

Conveniently, the probe and the seton have cooperating means to connect the probe to the seton end-to-end.

The probe and the seton may each terminate in an end face and their respective end faces face each other when connected together.

In one embodiment, the seton is swaged to the probe such that the seton and the probe are fused together. Conveniently, the seton is swaged or fused to the probe by melting an end of the seton and an end of the probe and by locating the two melted ends against one another. Thus, the ends blend together such that when the ends have cooled down, a bond is created between the seton and the probe.

The probe may be formed with a hollow end and an end portion of the seton locates in the hollow end of the probe, the connectable ends of the seton and the probe being fused together.

Similarly, the seton may be formed with a hollow end and an end portion of the probe locates in the hollow end of the seton, the connectable ends of the seton and the probe being fused together.

In another embodiment, the probe is formed with a hollow end and an end portion of the seton locates in the hollow end of the probe, the hollow end of the probe being configured to tightly fit around the end portion of the seton.

Similarly, the seton may be formed with a hollow end and an end portion of the probe locates in the hollow end of the seton, the hollow end of the seton being configured to tightly fit around the end portion of the probe.

According to a fourth aspect of the present invention, there is provided a device comprising a probe and a seton suitable for treating a fistula, wherein, the probe and the seton have cooperating means to releasably connect the probe to the seton end-to-end.

It follows from the fourth aspect of the present invention that further aspects of the present invention may provide a probe adapted for use in the fourth aspect of the present invention, and/or a seton adapted for use in the fourth aspect of the present invention.

Typically, the probe and the seton each terminate in an end face and their respective end faces face each other when connected together In a preferred embodiment of the fourth aspect of the present invention, the device is also a device according to any of the first to third aspects of the present invention.

Preferably said cooperating means allow the probe and the seton to be repeatedly connected and disconnected, preferably by hand.

For instance, the probe and the seton may comprise a threaded screw and screw attachment means so as to enable the probe and the seton to be connected to each other.

In one embodiment of the fourth aspect of the present invention, the probe comprises a screw extending from an end and the seton comprises a hollow end for receiving the screw of the probe so that the seton can be connected to the probe. The hollow end of the seton may be threaded.

Alternatively, the probe comprises a hollow end and the seton comprises an end having a screw extending therefrom, the hollow end of the probe being threaded so that it can be screwed onto the screw of the seton.

In another embodiment of the fourth aspect of the present invention, the cooperating means click-fit.

For instance, an end of the seton may be formed with a protrusion having a flange and the probe may comprise a hollow end having a recess corresponding to the shape of the flange. Alternatively an end of the probe may be formed with a protrusion having a flange and the seton may comprise a hollow end having a recess corresponding to the shape of the flange.

Preferably, the flange and/or the hollow end is resilient, typically such that as the protrusion is pushed into the hollow end, temporary deformation occurs until the flange locates in the corresponding recess.

Preferably, the means of connection are configured such that the force required to remove the protrusion from the hollow end is greater than the force required to pull the probe and the seton through a fistula so as to avoid the seton from detaching from the probe as the seton is being fitted.

In any of the first to fourth aspects of the present invention, wherein the device comprises a probe, preferably, the probe and the seton each have an outer diameter, wherein the overall diameter of the connected probe and seton in the region of the connection does not exceed the sum of the outer diameters of said probe and seton. More preferably, the overall diameter does not exceed 2 times, or 1.5 times the outer diameter of said probe or seton. Most preferably, the overall diameter does not exceed the outer diameter of said probe or seton.

In one embodiment, the probe and the seton each have a longitudinal axis and when the probe and the seton are connected together end-to-end, the longitudinal axes extending through the end of the probe and the seton are approximately coaxial.

The body of the probe is preferably made from a malleable material with sufficient rigidity to act as a guide when passed through the fistula. For instance, suitably malleable metals or plastics may be used.

The probe is typically elongate in shape, with a rounded blunt end distal from the end connectable to the seton. In one embodiment, the probe is between 3 and 30 cm in length. More preferably the probe is between 4 and 20 cm in length. Most preferably the probe is between 5 and 15 cm in length. Optionally, the probe is between 0.1 and 5 mm in diameter. Preferably the probe is between 0.2 and 4 mm in diameter. Most preferably the probe is between 0.5 and 2 mm in diameter.

In a preferred embodiment of any of the first to fourth aspects of the present invention, the probe and the seton are connected together end-to-end.

According to a fifth aspect of the present invention, there is provided a device suitable for treating a fistula comprising a seton and an attachment device, the seton being formed with a first end and a second end that are securable to each other by the attachment device.

In a preferred embodiment of the fifth aspect of the present invention, the device is also a device according to any of the first to fourth aspects of the present invention.

Preferably, the first end of the seton is provided with the attachment device, the attachment device being configured to receive the second end such that the seton is formed into a loop.

In one embodiment of the fifth aspect of the present invention, the first end of the seton is provided with the attachment device and the second end is connectable to a probe. Optionally the second end is connected to a probe. The probe and the manner of connection of the seton to the probe are preferably as described in relation to any of the first to fourth aspects of the present invention.

Conveniently, the attachment device comprises a housing formed with an aperture, preferably arranged such that the aperture and the second end of the seton are formed with cooperating means so as to enable the second end of the seton to be inserted through the aperture but prevented from being withdrawn from the aperture.

In one embodiment, the cooperating means comprises ratchet teeth formed on the second end of the seton and a pawl formed on the aperture of the housing for engagement with said teeth.

Preferably, the ratchet teeth are formed along a length of the second end of the seton so as to permit the seton to be pulled through the aperture of the attachment device to the required extent.

In one embodiment of the fifth aspect of the present invention, the device is formed with one or more cooperating elements adapted to align the first end and the second end of the seton, preferably in a secure manner. Typically, the one or more cooperating elements are adapted to align the redundant second end of the seton to the first end of the seton after the second end of the seton has passed through the aperture of the attachment device.

For instance, said cooperating element may comprise a loop through which the second end of the seton may be thread so as to retain the second end of the seton against the first end. Optionally, the loop may be affixed to the seton adjacent to the attachment device, such that in use the redundant end of the seton that has passed through the aperture of the attachment device may be thread through the loop so as to align the redundant end against the first end of the seton.

Preferably, the first end of the seton is formed with cooperating elements and the second end of the seton is formed with corresponding cooperating elements such that the first end and the second end can be aligned, preferably in a secure manner. For instance, the first end and the second end of the seton may click together.

The cooperating elements enable the redundant end of the seton that has been passed through the aperture of the attachment device to be securely aligned to a portion of the seton adjacent to the housing. As the first and second ends of the seton are held in alignment by the cooperating means, the likelihood of the redundant end of the seton interfering with surrounding tissue is reduced.

In another embodiment of the fifth aspect of the present invention, where the first end of the seton is provided with the attachment device and the attachment device is configured to receive the second end such that the seton is formed into a loop, the attachment device comprises means for automatically tightening the loop.

Typically, the attachment device may automatically tighten the loop at a rate of between 0.01 and 2 cm per day. Preferably the attachment device automatically tightens the loop at a rate of between 0.05 and 1 cm per day. More preferably, the attachment device automatically tightens the loop at a rate of between 0.1 and 0.5 cm per day. Preferably, said rate of tightening occurs when the loop is thread through a fistula such as an anal fistula or a recto-vaginal fistula.

In one embodiment, the device may be spring-loaded.

Alternatively, the device may be fitted with a spring loaded cog which engages with corresponding teeth formed on the seton, so as to pull the seton through the attachment device after the attachment device has received the second end of the seton.

Alternatively still, the device may comprise a motor such as an electric or clockwork motor which acts on the seton, so as to pull the seton through the attachment device after the attachment device has received the second end of the seton.

In any of the above embodiments of the fifth aspect of the present invention, the attachment device may be provided with one or more holes for enabling it to be sutured to tissue.

According to a sixth aspect of the present invention, there is provided a device comprising a plug suitable for treating a fistula, wherein the plug is adapted to be secured to a seton. Preferably the plug is secured to a seton. Optionally, two or more such plugs may be secured to a seton.

In one embodiment of the sixth aspect of the present invention, the plug is approximately cylindrical or conical in shape. Typically, the plug may be from 1 to 20 cm long. Preferably, the plug is from 2 to 10 cm long. Most preferably, the plug is from 4 to 8 cm long.

Typically, the plug has an average diameter of from 2 to 10 mm. Preferably, the plug has an average diameter of from 5 to 7 mm.

Optionally, the plug may further comprise a flange located at one end of the plug. Typically, said flange extends beyond the diameter of the plug. Preferably, the flange is configured not to pass through the fistula, but to abut the tissue surface adjacent to the point of exit of the fistula, thereby aiding the secure positioning of the plug within the fistula.

In one embodiment the plug comprises a hole through which the seton may be thread. Preferably the hole runs parallel to the longitudinal axis of the plug or is coaxial with the longitudinal axis of the plug. Typically, the hole is between 0.1 and 5 mm in diameter. Preferably the hole is between 0.2 and 4 mm in diameter. Most preferably the hole is between 0.5 and 2 mm in diameter.

In another embodiment the plug comprises one or more holes to enable the plug to be sutured to the seton. Preferably the plug comprises a plurality of such holes dispersed along the length of the plug.

In yet another embodiment, the plug is formed with cooperating elements such that in use, the plug may be secured to a seton with corresponding cooperating elements.

In a preferred embodiment of the sixth aspect of the present invention, the plug comprises a tissue growth promoting matrix, such as any outlined for use in relation to the first aspect of the present invention. Most preferably the plug is formed from fibrin and/or collagen.

In any embodiment of any aspect of the present invention, it is preferred that the seton and/or the device as a whole is made from biocompatible materials.

For instance, where the seton or a segment thereof is not biodegradable, it may be formed from flexible materials such as rubber, silicone, silk, flexible plastics such as polypropylene and the like.

Preferably the segment of the seton to be positioned within the fistula does not contain exposed metal. More preferably, the segment of the seton to be positioned within the fistula does not contain metal. Most preferably, the seton does not contain metal.

Typically, in any embodiment of any aspect of the present invention, the seton is between 5 and 100 cm in length. More preferably the seton is between 10 and 50 cm in length. Most preferably the seton is between 15 and 30 cm in length. Typically, the seton is between 0.1 and 5 mm in diameter. Preferably the seton is between 0.2 and 4 mm in diameter. Most preferably the seton is between 0.5 and 2 mm in diameter.

In one embodiment of any aspect of the present invention, the device may further comprise one or more washers. The seton may be thread through and optionally attached to said washers. In use the washers are preferably positioned adjacent to the portion of the seton that passes through the fistula, such that they abut the tissue surface adjacent to the point of exit of the fistula.

According to a seventh aspect of the present invention, there is provided a device according to any of the first to sixth aspects of the present invention, for use in medicine. Preferably said device is for use in the treatment of a fistula such as an anal fistula or a recto-vaginal fistula.

As used herein, a "fistula" refers to any abnormal passage or communication through the body between two epithelial surfaces, including those occurring naturally, e.g. as a result of infection, those occurring as a result of injury, e.g. as a result of impalement, and those man-made, for example as a result of surgery or body piercing.

In a preferred embodiment of any aspect of the present invention, the fistula to be treated is selected from:
(i) a body piercing or skin-to-skin fistula;
(ii) an anal or anorectal fistula, which may be classified anatomically as intersphincteric, transphincteric, suprasphincteric or extrasphincteric;
(iii) a recto-vaginal fistula such as an anovulval, anovaginal, rectovulval, rectovaginal or rectovestibular fistula, wherein the recto-vaginal fistula may be classified anatomically as infrasphincteric, transphincteric, or suprasphincteric;
(iv) a recto-prostatic fistula;
(v) a gastrointestinal fistula such as a *trachea*-oesophageal, gastro-cutaneous, ileo-cutaneous, colo-cutaneous, colo-vaginal or gastrointestinal-vascular fistula; or
(vi) a urinary fistula such as a urethrocutaneous, urethrovaginal, urethrovesical, vesciovaginal, rectovesical or rectourethral fistula.

Typically said fistulas are complete (i.e. both ends open on a mucosal or exterior surface of the body). Complete fistulas may be external (i.e. between a hollow organ and an external surface of the body) or bimucosal (i.e. both ends open on a mucosal surface of the body).

Preferably said fistulas are simple (i.e. contain no blind tracts and contain only one opening at each end of the tract). Optionally however said fistulas include blind tracts and/or are complex (i.e. include more than two openings due to division of the tract). An example of a complex fistula is a horseshoe fistula (where two ends of the fistula tract open on an exterior surface of the body and a third end opens into a hollow organ such as the anal canal).

More preferably, the fistula to be treated is selected from an anal fistula or a recto-vaginal fistula. Most preferably the fistula is an anal fistula According to an eighth aspect of the present invention, there is provided a method of treating a fistula comprising the use of a device according to any of the first to sixth aspects of the present invention. Preferably the fistula is an anal fistula or a recto-vaginal fistula. Preferably said method comprises inserting the seton and/or the plug into the fistula. Most preferably said method comprises inserting a tissue growth promoter into the fistula and securing the tissue growth promoter using a seton.

According to a ninth aspect of the present invention, there is provided a seton for use in the treatment of a fistula, said treatment comprising the use of the seton to secure a tissue growth promoter.

According to a tenth aspect of the present invention, there is provided a tissue growth promoter for use in the treatment of a fistula, said treatment comprising the use of a seton to secure the tissue growth promoter.

According to an eleventh aspect of the present invention, there is provided a method of treating a fistula comprising the use of a seton to secure a tissue growth promoter.

The tissue growth promoter and the seton of any of the ninth to eleventh aspects of the present invention are preferably as described in relation to any of the first to sixth aspects of the present invention.

Preferably the patient to be treated in any of the preceding aspects of the invention is a human. Optionally, the patient may also be suffering from an inflammatory bowel disease such as Crohn's disease.

For the avoidance of doubt, insofar as is practicable any embodiment of a given aspect of the present invention may occur in combination with any other embodiment of the same aspect of the present invention. In addition, insofar as is practicable it is to be understood that any preferred or optional embodiment of any aspect of the present invention should also be considered as a preferred or optional embodiment of any other aspect of the present invention.

DETAILED DESCRIPTION OF THE INVENTION

Embodiments of the present invention will now be described by way of example only, with reference to the accompanying drawings, in which.

The devices of the present invention are particularly useful for the treatment of fistulas such as anal or recto-vaginal fistulas. Depending on the fistula to be treated however, it may be desirable and/or necessary to pre-treat the fistula prior to the use of the devices of the present invention. For instance, if the fistula is heavily infected, it may be desirable to insert a drainage seton according to the prior art methods discussed above. The drainage seton may optionally incorporate antibiotics and/or anti-inflammatories in order to help reduce the extent of infection. After a period of time the drainage seton may be removed prior to the insertion of a device according to the present invention.

Optionally, prior to the insertion of a device according to the present invention, the fistula tract may be cleaned, for example using a jet of water and/or a suitable brush.

Figure 1:
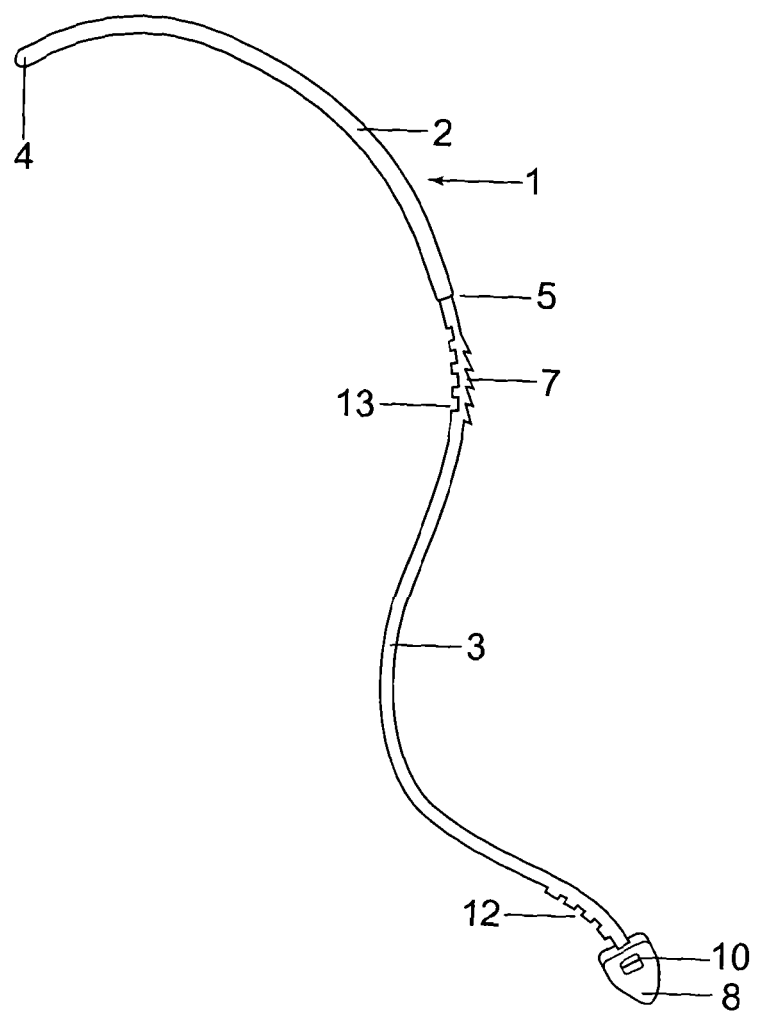
FIG. 1 shows a planar view of a device comprising a probe and seton according to the present invention.

Referring now to FIG. 1, there is shown a device 1 according to an embodiment of the present invention comprising a probe 2 and a seton 3 for assisting in the healing of fistulas.

The probe 2 comprises an elongate body having a blunt end 4 and an opposite end 5 to which the seton 3 is attached. The probe 2 is inserted into the fistula with the blunt end first such that the surgeon can use the probe to discover the track of the fistula. The end 4 is blunt rather than sharp so as to reduce damage to surrounding tissue and to minimise the possibility of the probe going off track creating false passages.

The probe 2 is made out of a malleable metal or plastic that is easily bent so that it can be formed into a desired shape by the surgeon. This enables the surgeon to tailor the shape of the probe 2 to the track of the fistula so that the probe 2 can more easily be fed through the fistula with minimal damage to surrounding tissue. The probe 2 may vary in size depending on the type of fistula that is to be treated. It is envisaged that the probe is between 6 to 12 cm long and 0.5-2.0 mm in diameter.

The seton 3 is in the form of a flexible thread and is preferably made out of a tough flexible rubber or plastic such as polypropylene, in particular when treating fistulas wherein the seton has to be left in position for a longer period of time. Alternatively, the seton 3 may be formed out of a biodegradable material such as polyglycolic acid such that the seton 3 biodegrades in situ with time, thereby obviating the need to remove the seton 3 from the treatment site.

The end 5 of the probe 2 opposite to the blunt end 4 is hollow and an end portion of the seton 3 locates therein and is secured to the probe 2 by the end 5 of the probe 2 being reduced in diameter such that a tight fit is created between the end 5 of the probe and the end of the seton 3. The diameter of the end 5 of the probe may be reduced by passing the end 5 of the probe through an aperture of a die. The aperture is configured to be of a smaller diameter than the initial diameter of the end 5 of the probe. The diameter of the end 5 of the probe can also be reduced by shaping the end 5 by hammering. Alternatively, the end of the seton 3 may be swaged to the corresponding hollow end of the probe 5 such that the seton 3 and the probe 5 are fused together end-to-end.

In an alternative embodiment, the end 5 of the probe opposite to the blunt end 4 may be solid such that an end face of the probe is directly swaged or fused to an end face of the seton 3. All of the aforementioned methods securely attach the seton 3 to the probe 2 such that as the surgeon feeds the probe 2 through the fistula the seton 3 follows the probe without detaching. In contrast, a seton that is threaded through an eye of a probe as known from the prior art may easily detach as it is pulled through the fistula such that the surgeon may have to repeat the process causing further discomfort to the patient.

As can be appreciated from FIG. 1, at the point of attachment of the seton 3 and the probe 2, the longitudinal axis of the seton 3 is aligned with the longitudinal axis of the probe 2 and the overall diameter of the device in the region of the connection does not exceed the diameter of the probe 2. The region of the connection should be understood to mean the region where the seton engages with the probe, in particular where the seton is swaged to the probe or where a tight fit is created between the seton and the probe. Preferably, the region of the connection of the aforementioned embodiments is less than 2 cm in a direction parallel to the longitudinal axis of the seton and the probe.

The features of the longitudinal axis of the seton 3 being aligned with the longitudinal axis of the probe 2 and/or the overall diameter of the device in the region of the connection not exceeding the diameter of the probe 2, minimise damage to surrounding tissue when the probe 2 and the seton 3 are fed through the fistula in contrast to devices known from the prior art wherein the seton is thread through an eye of a probe. That is, because as a seton is thread through an eye of a probe it is transverse to the longitudinal axis of the probe and as a result of resilient characteristics of the seton, the transverse portion of the seton thread through the eye of the probe may extend beyond the diameter of the probe thereby abrading the surrounding tissue as the probe and the seton are fed and pulled through the fistula.

Furthermore, as the seton is thread through the eye of the probe a double layer of the seton is formed which also may extend beyond the diameter of the probe. As discussed in the introduction, it is also known from the prior art to overlap an end of the seton with an end of the probe and thereafter to lash or suture the ends together. The overall diameter of the region in which the seton and the probe are connected is therefore bulky and extends beyond the diameter of the probe. Again, this may abrade and damage surrounding tissue as the probe and the seton are fed and pulled through the fistula.

The seton 3 of the present invention is optionally secured to the probe 2 by any of the methods discussed herein during manufacturing so that the surgeon is not required to assemble the seton 3 and the probe 2 prior to use. For instance, the seton may be glued or welded onto the probe. Therefore, the device 1 is easier to use than those known from the prior art which require the surgeon to carefully thread or tie the seton to the probe. Furthermore, the fact that the device is pre-assembled reduces the required surgical preparation time.

As best shown in FIG. 1, on one side of the seton 3 proximal to its attachment to the probe 2 ratchet teeth 7 are formed. In FIG. 1 (and also FIGS. 2 and 4-6), the ratchet teeth 7 are shown to protrude from the seton 3 such that they extend beyond the diameter of the seton 3. In an alternative embodiment, it is envisaged that the ratchet teeth do not extend beyond the diameter of the seton. This may be achieved by making or moulding incisions into the seton transversely to the longitudinal axis of the seton so as to form ratchet teeth.

Figure 2:
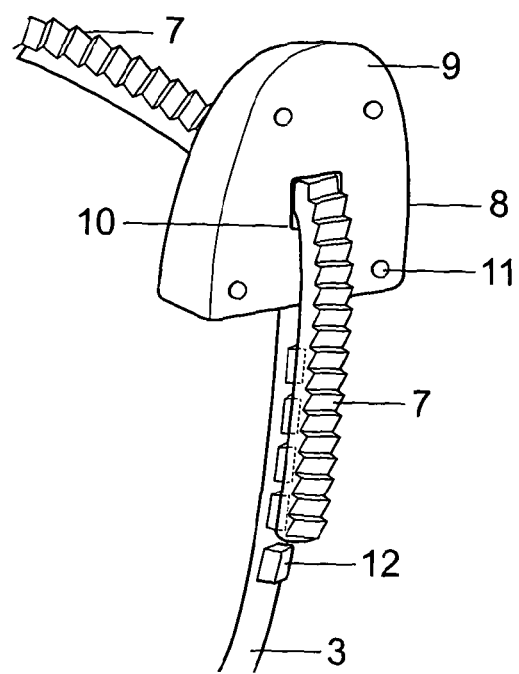
FIG. 2 shows a perspective view of a locking device of the device in FIG. 1.

The ratchet teeth 7 engage with a locking device 8 also referred to as an attachment device as shown in FIGS. 1 and 2. The locking device 8 comprises a housing 9 formed with an aperture 10 that is transverse to the plane of the housing 9. A resiliently deformable pawl (not shown) extends into the aperture 10 for engagement with the ratchet teeth 7 when the seton 3 is inserted through the aperture 10, such that the seton 3 cannot be withdrawn from the aperture 10.

It is envisaged that once the surgeon has inserted the probe 2 and the seton 3 through the fistula such that either ends of the seton 3 extend from either ends of the fistula, the surgeon feeds the blunt end 4 of the probe 2 followed by the seton 3 through the aperture 10 of the locking device 8 so as to form a loop. Thereafter, the surgeon cuts the seton 3 proximal to the probe 2. In an alternative method, the surgeon may cut the seton 3 adjacent to the probe and thereafter feed the free end of the seton 3, provided with ratchet teeth 7, through the aperture of the locking device 8. In either method, cooperation between the ratchet teeth 7 and the pawl permits the seton 3 to be pulled through the aperture 10 of the locking device 8 to the required extent.

By the locking device 8 securing the opposite end of the seton 3 so as to form a loop, the seton 3 remains in its position throughout the treatment period. Therefore, the problem of a knot securing the seton becoming undone as known from the prior art is overcome and so the probability of the surgeon having to re-insert a seton is reduced.

The ratchet teeth 7 and the locking device 8 enable the seton 3 to form a loop of variable size, as the seton can be pulled through and secured to the locking device at any desired length where the ratchet teeth 7 are formed. Therefore, the device 1 can be specifically adjusted to individual patients and their needs.

As can be appreciated from FIG. 2, the housing 9 of the locking device 8 is formed with four holes 11. These holes enable a surgeon to suture the locking device 8 to the wall of the anal canal. Advantageously, as the seton 3 is held in place and the locking device 8 is retained internally, discomfort caused by a knot of two tied ends of a seton as known from the prior art is overcome.

A portion of the seton 3 adjacent to the locking device 8 is formed with a coupling element so as to be secured to a corresponding coupling element formed at the same end as the ratchet teeth 7. In the illustrated embodiment shown in FIGS. 1 and 2, the coupling elements of the seton 3 comprise protrusions 12 formed adjacent to the locking device 8 and corresponding recesses 13 formed on the opposite side of the ratchet teeth 7. The protrusions 12 are a friction fit within corresponding recesses 13 to secure the end of the seton 3 that has been passed through the aperture 10 of the locking device 8, to a portion of the seton 3 adjacent to the ratchet teeth 7. The redundant end of the seton 3 is thereby aligned with the remaining seton 3 and any excess cut off.

It will be appreciated that the coupling elements of the seton 3 are optional. Alternative means for attaching the redundant end of the seton to the end of the seton proximal to the locking device may be used or omitted altogether.

It should be understood by those skilled in the art that the present invention is not limited to the locking device described above. Any locking device that securely holds the two loose ends of the seton together falls within the scope of the present invention.

An alternative embodiment will now be described with reference to FIG. 3. The configuration of this embodiment only differs to the aforementioned embodiment in how the seton is attached to the probe and so a general description of the device will be omitted.

Figure 3:
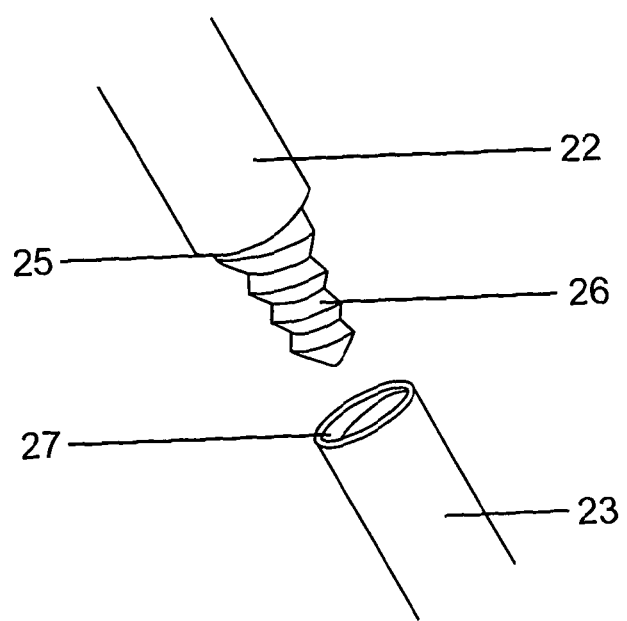
FIG. 3 shows a perspective view of an alternative embodiment of the connection between the seton and the probe shown in FIG. 1.

In FIG. 3, an end 25 of a probe 22 is shown. The end 25 is formed with a threaded screw 26 for receiving a seton 23. The screw 26 extends from the end 25 of the probe 22 and its longitudinal axis is aligned with the longitudinal axis of the probe and its diameter is preferably smaller than that of the probe 22. Preferably, the probe 22 and the screw 26 are integrally formed. The seton 23 is formed with corresponding screw attachment means in that it has a hollow end 27. Although the hollow end 27 of the seton 23 is not threaded it is screwed onto the screw 26 by the flexible nature of the material used for the seton 23. In an alternative embodiment, the internal surface of the hollow end 27 of the seton 23 is threaded so that the seton 23 is screwed onto the threaded screw 26 of the probe 22.

It shall be understood that the threaded screw may alternatively be formed on an end of the seton and the probe may be formed with a corresponding threaded screw attachment means such as a hollow end so that the probe can be screwed onto the seton. In this embodiment, the seton and the screw may be integrally formed.

The aforementioned embodiments described with reference to FIG. 3, have the same advantages as those described with reference to FIG. 1. In particular, as the longitudinal axis of the probe and the longitudinal axis of the seton are aligned at the point of attachment the probability of damaging surrounding tissue as the probe and seton are pulled through is reduced. This is also achieved by the fact that the diameter of the screw is smaller than the diameter of the probe and the seton so that as the seton and the probe are connected, the outer surfaces of the probe and the seton are flush or the diameter of the seton is smaller than that of the probe. As a result, the diameter of the region of the connection does not exceed the overall diameter of the device. The region of connection should be understood to mean the region where the screw is received in the corresponding screw attachment means. Preferably, the region of the connection of the seton and the probe of the present embodiments is less than 2 cm in a direction parallel to the longitudinal axis of the seton and the probe.

It should be appreciated that the seton of the device according to the present invention can be secured to the probe by alternative means than those described hereinbefore. For example, the seton and the probe may be secured by 'click fitting'. In this un-illustrated embodiment, an end of the seton may be formed with a protrusion having a resilient flange and the probe may comprise a hollow end having a recess corresponding to the shape of the flange. By inserting the protrusion of the seton into the hollow end of the probe, the flange temporarily deforms until it locates in the corresponding recess. In this embodiment, the means of connection are configured such that the force required to insert the protrusion of the seton into the hollow end of the probe is greater than the force required to pull the probe and the seton through a fistula so as to avoid the seton from detaching from the probe as the seton is being fitted.

An advantage of the probe and the seton being releasably connectable, such as by means of the screw attachment or click-fitting described above, is that in use the surgeon can rapidly interchange probes without having to undertake the fiddly and time-consuming task of threading the seton through an eye of the probe. Furthermore, where it is desired to treat complex fistulas such as horseshoe fistulas, the use of two or more setons may be required. In such a scenario, a further advantage of the probe and the seton being releasably connectable is that a single probe may be used for the insertion of both setons, thus saving on the equipment required and hence the cost of the procedure.

In another un-illustrated embodiment, the device is spring loaded so that the seton will retain a snug fit through the fistula for an extended period of time. Often, for a seton to promote optimal healing of a fistula, it is desirable for the seton to be snugly fitted throughout the treatment period. This is particularly important in cases where the seton is used to gradually cut through the sphincter muscle. However, setons as known from the prior art may become slack as they gradually cut through the sphincter muscle resulting in the seton becoming less effective in dividing the remaining muscle tissue. To overcome this problem, the device according to the present invention may be spring loaded so as to absorb any slacking so that the seton is continuously snugly fitted through the fistula for a desired period of time. Preferably, a spring is fitted between the locking device and the seton so as to absorb any slacking. Alternatively, the device may be fitted with a spring loaded cog which engages with corresponding teeth formed on the seton. The cog could be configured to comprise a coil spring and preferably the cog would engage with the redundant end of the seton that has been pulled through the locking device such that the cog pulls the seton through the locking device as the seton starts to slack.

A preferred embodiment is now described which may comprise any combination of individual features as described above. In this embodiment the seton is provided with a tissue growth promoter such as fibrin so as to further promote tissue repair of the fistula. The seton may further be provided with one or more additional pharmaceutical agents so as to reduce inflammation or infection by locally delivering the specific agents to the treatment site. In this manner, many of the drawbacks associated with systemic drug delivery are avoided and relatively high concentrations of the required pharmaceutical agent can be targeted at the point of need with minimal side effects.

In one embodiment, the seton is provided with fibrinogenic materials which include any material based on fibrin. The seton may be coated directly in fibrinogenic material or the fibrinogenic material may be incorporated into a biodegradable polymer such as alginate which coats the seton.

Figure 4:
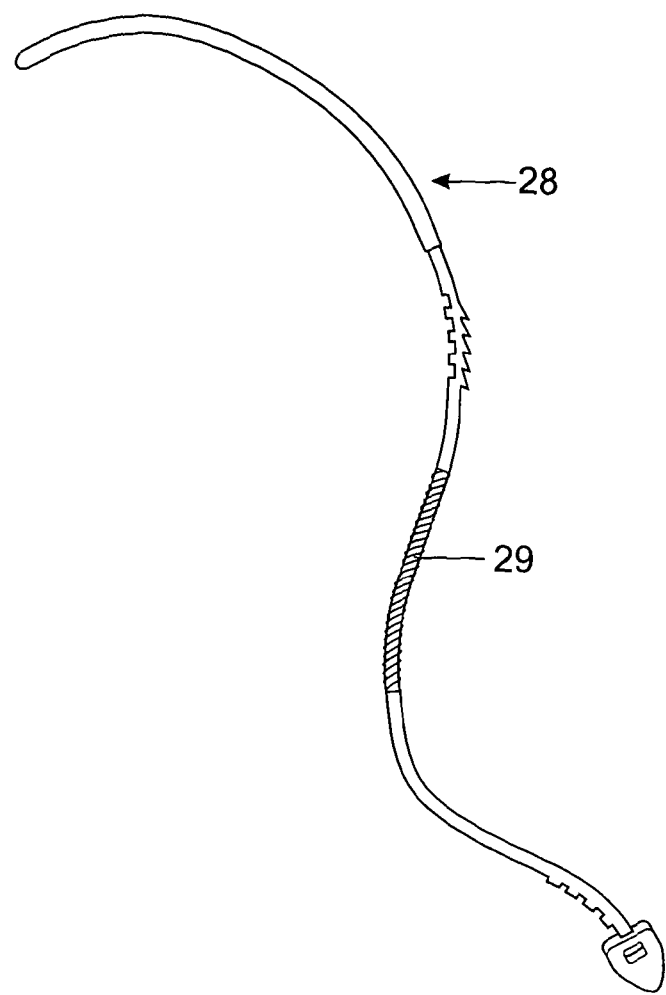
FIG. 4 shows a planar view of an embodiment of the device wherein a segment of the seton comprises a tissue growth promoting matrix.

Alternatively, as illustrated in FIG. 4, a segment 29 of the seton may itself be made from a tissue growth promoting matrix such as fibrin, with the remainder of the device 28 being as described in relation to FIG. 1.

Thus, in use the portion of the seton being made from or provided with a tissue growth promoter is positioned within the fistula tract so as to encourage tissue growth therein.

It is envisaged that fibrinogenic material can best be used in cases where there has been no active sepsis, that is to say when the tract of the fistula is a single tunnel with no blind tracts and no intervening abscess cavity in the path of the fistula.

Figure 5:
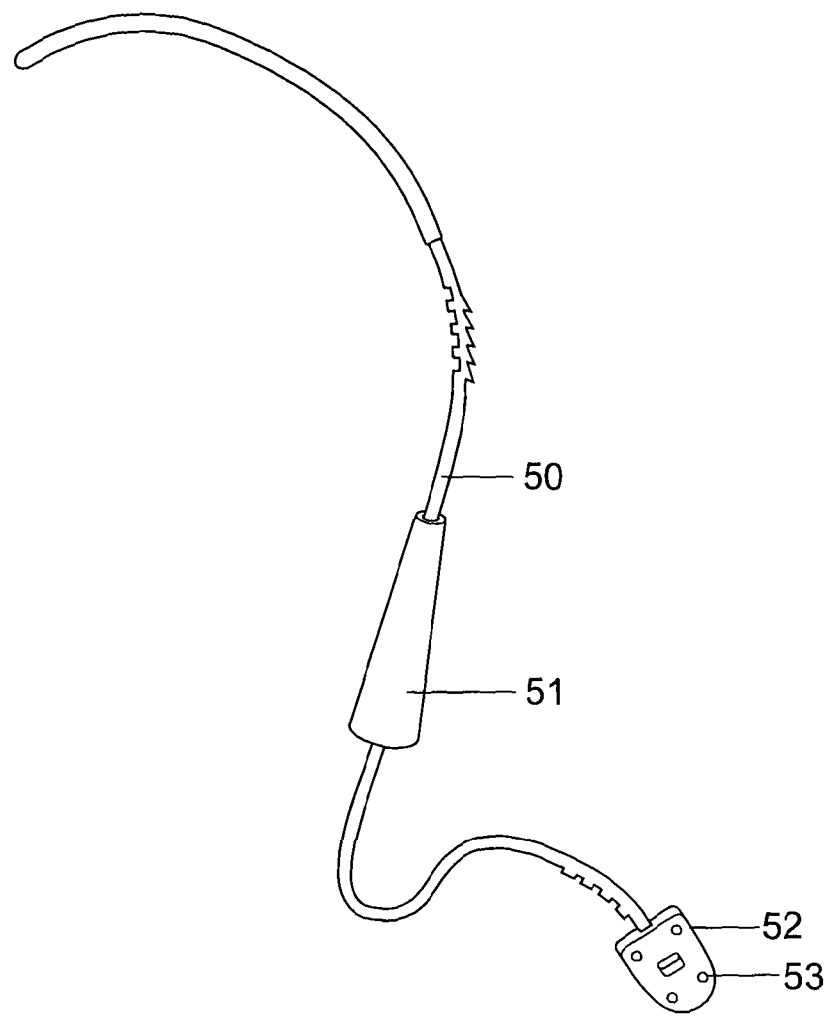
FIG. 5 shows a planar view of an embodiment of the device comprising a fibrin plug thread onto the seton.

In another embodiment, the seton may be provided with a fibrin plug, as illustrated in FIG. 5. For example, the seton 50 may be threaded through the centre of a fibrin plug 51 commercially sold as Biodesign® and manufactured by Cook® Medical. The seton is thus able to hold the fibrin plug firmly in place. When used in conjunction with the previously described locking device 52, the seton and hence the fibrin plug may be further secured in an exact position by the use of sutures through the holes 53.

Figure 6:
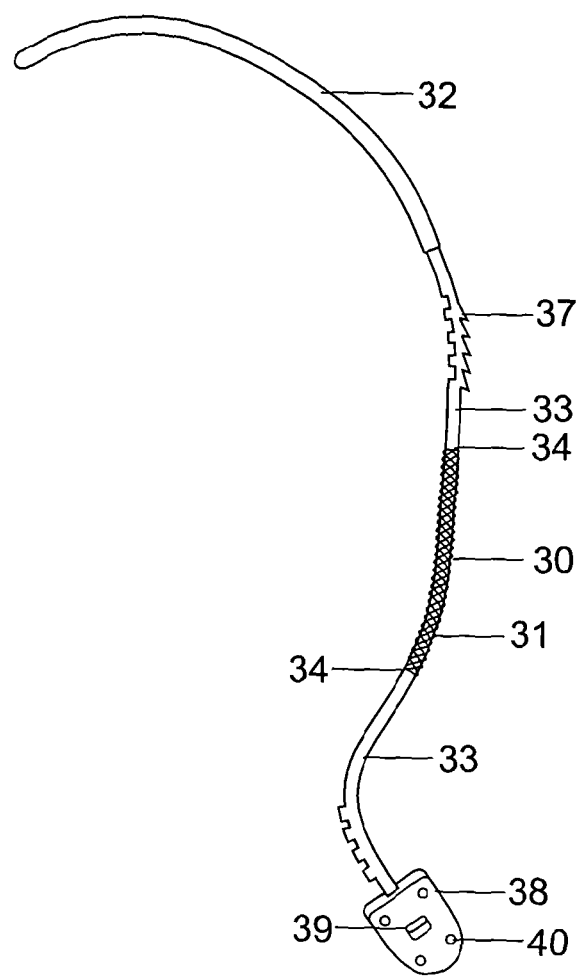
FIG. 6 shows a planar view of an embodiment of the device comprising an enclosure holding pharmaceutical agents.

Referring now to FIG. 6, a cage 30 is shown which is attached to the seton 33. The cage 30 is made out of a biodegradable material and it comprises a wall 31 shaped into a hollow cylinder. The wall 31 is formed out of a mesh so as to allow tissue in-growth and efficient release of pharmaceutical agents. The cage 30 is also formed with means of attachment 34, for example screws, on either end. A portion of the seton 33 is attached to either end of the cage 30 via the means of attachment 34. One portion comprises the locking device 38 and the cooperating elements and the other portion comprises the ratcheting 37 and the corresponding cooperating elements as described in relation to the aforementioned embodiments. The cage 30 defines a space for holding pharmaceutical agents such as a fibrin plug (not shown), for example the fibrin plug manufactured by Cook® Medical, or pellets of fibrinogenic material. The fibrin plug or any other pharmaceutical material that is to be used is inserted into the cage prior to attaching the portions of seton 33 to the means of attachment 34. Thus, access to the inside of the cage is either at one or other end at the point of attachment 34 of the cage to the seton 33. Alternatively, it could be in the middle of the cage using a separate screw attachment device not shown or numbered in FIG. 6. The seton 33 provided with the cage 30 is inserted through a fistula using a probe 32 in a similar way as described above. The seton is cut proximal to the probe and is secured by inserting the freed end of the seton 33 through the aperture 39 of the device. Preferably, the locking device 38 is formed with holes 40 so that the locking device 38 can be sutured to the wall of the anal canal which thereby prevents the loop of seton 33 from moving or rotating. The advantage of the seton 33 being provided with a cage 30 is that it retains the fibrin plug in its position throughout the treatment period thereby promoting primary healing.

Preferably, the seton provided with fibrinogenic materials or a fibrin plug with or without a cage is formed out of biodegradable material. After a period of time, typically 4 to 6 weeks, this allows for the seton to be cut off at the entry and exit points of the fistula such that a segment of the seton and the fibrin with or without a cage remain in the fistula as they are gradually broken down by the body and fully or partially replaced by new tissue formation.

Depending on the type of fistula to be treated the fibrinogenic material and the fibrin plug with or without the cage may extend for a length of 2 to 6 cm, and preferably for a length of 3 to 5 cm. The cage is preferably 2.5 mm in diameter.

In some embodiments, the seton may further be provided with antibiotics, anti-inflammatories such as steroids or tumour necrosis factor (TNF) inhibitors, or immunomodulators and the like. A seton provided with antibiotics such as gentamicin would be used for treating local septic areas of the fistula, thereby avoiding or reducing systemic side effects associated with oral medication. A seton provided with steroids or immunomodulators would be particularly useful in patients suffering from Crohn's disease where local treatment of affected tissue may increase the rate of tissue regeneration and potentially reduce any systemic side effects resulting from oral medication. Similarly, a seton provided with a TNF inhibitor would provide effective targeting of tumour cells in the area of the fistula.

For the embodiments described above wherein the seton is provided with one or more tissue growth promoters and/or pharmaceutical agents, it is preferred to suture the locking device to the anal wall. This ensures that the portion of the seton provided with active agents is always located in the fistula and prevents the loop of the seton from rotating.

Figure 7:
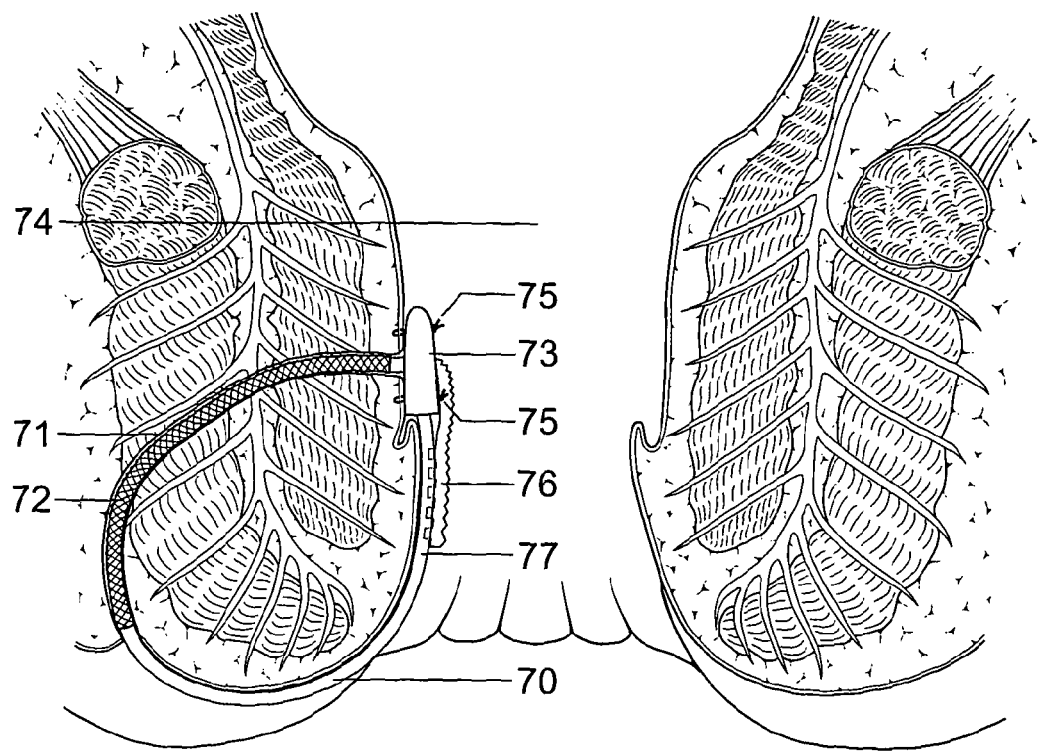
FIG. 7 shows a schematic diagram of a seton of the present invention positioned within an anal fistula.

Referring to FIG. 7, a schematic diagram of a seton 70 of the present invention positioned within an anal fistula 71 is illustrated. A segment 72 of the seton 70 provided with a tissue growth promoter is secured within the anal fistula 71. The seton loop is held together by means of the attachment device 73 which is positioned within the anal canal 74.

The attachment device is sutured to the wall of the anal canal by means of sutures 75 so as to prevent displacement of the tissue growth promoting segment out of the fistula by rotation of the seton loop. The redundant second end 76 of the seton that has passed through the attachment device and from which the probe has been removed is securely aligned against the first end 77 of the seton by means of the previously described cooperating elements. Discomfort to the patient caused by loose ends of the seton is thereby avoided.

By securely positioning the tissue growth promoting segment 72 within the fistula 71 by means of the seton 70, tissue in-growth is encouraged, thereby allowing the fistula to heal.

Furthermore, the seton ensures that the tissue growth promoter is robustly held in place within the fistula, thus the problems encountered in the prior art due to fistula plugs falling out of the fistula are obviated.

Figure 8:
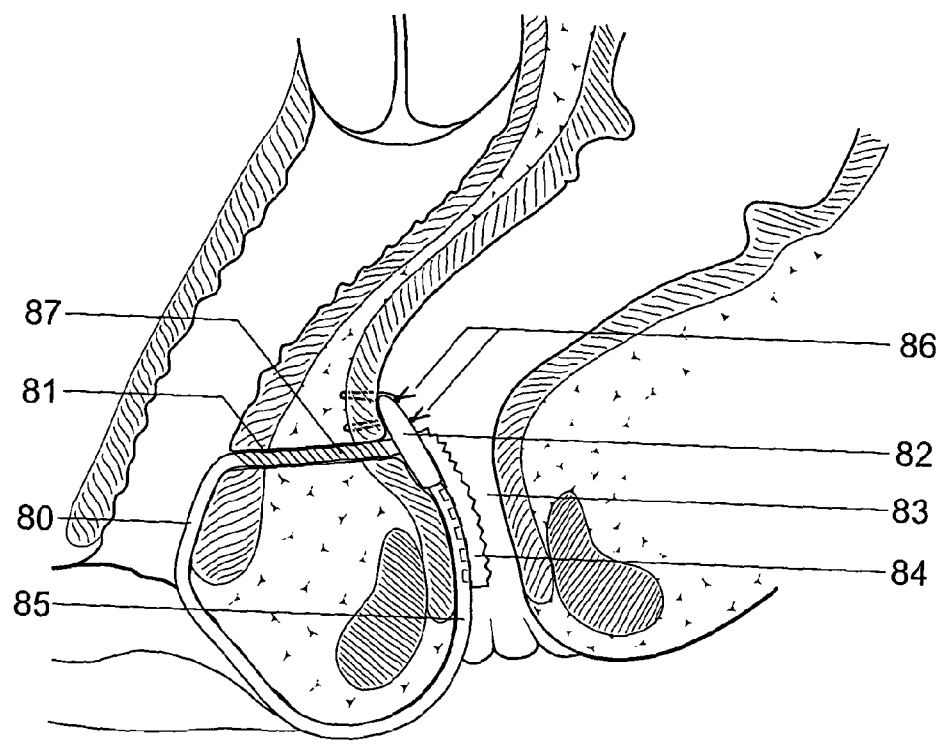
FIG. 8 shows a schematic diagram of a seton of the present invention positioned within a recto-vaginal fistula.

Finally, referring to FIG. 8 a schematic diagram of a seton 80 of the present invention positioned within a recto-vaginal fistula 81 is illustrated.

Thus, in use the seton 80 attached to the probe (not shown) may be thread through the recto-vaginal fistula 81 from the vaginal opening and then through the attachment device 82 attached to the other end of the seton, which may be located inside the anal canal 83 so as to secure the seton loop. The probe may then be cut off and the redundant end 84 of the seton that has passed through the attachment device may be securely aligned against the other end 85 of the seton by means of cooperating elements. The attachment device may be sutured to the wall of the anal canal by means of sutures 86.

Accordingly, it can be seen that a segment 87 of the seton 80 provided with a tissue growth promoter is secured within the recto-vaginal fistula 81. Thus, tissue in-growth is encouraged, thereby allowing the fistula to heal. Typically, after a 4 to 6 week healing period, the seton is cut proximal to the entry and exit of the fistula, so as to leave the absorbed tissue growth promoter within the fistula tract whilst allowing the attachment device and the remainder of the seton to be removed.

Of course, it will be appreciated that the devices according to the present invention may be used by the person skilled in the art to treat simple anal and recto-vaginal fistulas using variations of the techniques exemplified above. For instance, when used to treat a recto-vaginal fistula, the probe may be thread through the recto-vaginal fistula from the rectal opening and/or the attachment device may be sutured to the wall of the vagina.

Similarly, it will be appreciated that whilst uses of the devices according to the present invention have been described above in relation to simple anal and recto-vaginal fistulas, the person skilled in the art will understand that the devices may also find application in many other types of fistula.

The devices of the present invention find particular application in fistulas adjacent to which there is a substantial body of tissue about which the seton loop may be affixed. Preferably the fistulas to be treated comprise or are located near at least one external opening such that the seton loop lies partially outside of the body. That said however, the use of the devices of the present invention entirely internally is also envisaged.

Furthermore, the devices and the uses described may be best adapted by the surgeon in view of the particular fistula to be treated. For instance, where a fistula is complex, two or more such devices may be used to ensure that a tissue growth promoter is positioned within each tract.

Although embodiments of the invention have been shown and described, it will be appreciated by those persons skilled in the art that the foregoing description should be regarded as a description of preferred embodiments only. The examples are not intended to limit the scope of the invention. Various modifications and embodiments can be made without departing from the scope and spirit of the invention, which is defined by the following claims only.

The invention claimed is:

1. A method of treating a fistula comprising securing a tissue growth promoter within a fistula with a seton that extends through the fistula and outside the fistula from a first end of the fistula around a body of tissue adjacent to the fistula to a different second end of the fistula, forming a seton loop securing the tissue growth promoter within the fistula, thereby encouraging tissue ingrowth and allowing healing of the fistula.

2. A method according to claim 1, wherein the seton loop lies partially outside of the body.

3. A method according to claim 1, wherein the fistula is an anal fistula or a recto-vaginal fistula.

4. A method according to claim 1, wherein the tissue growth promoter comprises a tissue growth promoting agent.

5. A method according to claim 4, wherein the tissue growth promoting agent is a growth factor.

6. A method according to claim 5, wherein the growth factor is selected from basic fibroblast growth factor (FGF-2), transforming growth factor beta (TGF-beta), epidermal growth factor (EGF), cartilage derived growth factor (CDGF), platelet derived growth factor (PDGF), insulin-like growth factor I or II (IGF-I or IGF-II), an interferon, or a mixture thereof.

7. A method according to claim 1, wherein the tissue growth promoter comprises a tissue growth promoting matrix.

8. A method according to claim 7, wherein the tissue growth promoting matrix comprises a microscopic scaffold.

9. A method according to claim 7, wherein the tissue growth promoting matrix comprises fibrin and/or collagen.

10. A method according to claim 7, wherein the tissue growth promoting matrix comprises a macroscopic scaffold.

11. A method according to claim 10, wherein the macroscopic scaffold comprises a plurality of interwoven and/or interconnected strands.

12. A method according to claim 10, wherein the macroscopic scaffold is made from a biodegradable polymer.

13. A method according to claim 12, wherein the biodegradable polymer is a polylactide, a polyglycolide or a poly(lactide-co-glycolide).

14. A method according to claim 7, wherein a segment or all of the seton consists of a tissue growth promoting matrix.

15. A method according to claim 7, wherein a tissue growth promoting matrix is attached to the seton.

16. A method according to claim 7, wherein the seton is thread through a tissue growth promoting matrix.

17. A method according to claim 1, wherein the treatment further comprises the use of one or more additional pharmaceutical agents.

18. The method of claim 17, wherein the one or more additional pharmaceutical agents are selected from anti-inflammatories, anti-bacterial agents, immunomodulators, and combinations thereof.

19. A method according to claim 1, wherein the seton comprises a biodegradable material.

20. A method according to claim 19, wherein the tissue growth promoter comprises a tissue growth promoting matrix located inbetween biodegradable portions of the seton.

21. A method according to claim 1, wherein the seton comprises a flexible non-biodegradable material.

* * * * *